(12) United States Patent
Molenda et al.

(10) Patent No.: US 8,048,836 B2
(45) Date of Patent: Nov. 1, 2011

(54) HAIR STYLING COMPOSITION COMPRISING AN ARYLATED SILICONE

(75) Inventors: Michael Molenda, Frankfurt (DE); Martin Hoffmann, Zwingenberg (DE); Jutta Klutzny, Darmstadt (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 0 days.

(21) Appl. No.: 12/187,038

(22) Filed: Aug. 6, 2008

(65) Prior Publication Data
US 2009/0041683 A1  Feb. 12, 2009

(51) Int. Cl.
C11D 9/36 (2006.01)
C11D 3/37 (2006.01)

(52) U.S. Cl. ........ 510/122; 510/119; 510/466; 510/475; 510/476; 510/140

(58) Field of Classification Search .................. 510/122, 510/119, 466, 475, 476, 140
See application file for complete search history.

(56) References Cited

U.S. PATENT DOCUMENTS

| | | | | |
|---|---|---|---|---|
| 4,764,363 A * | 8/1988 | Bolich, Jr. | | 424/47 |
| 4,834,968 A * | 5/1989 | Bolich, Jr. | | 424/47 |
| 5,154,849 A * | 10/1992 | Visscher et al. | | 510/150 |
| 5,169,623 A * | 12/1992 | Kopolow et al. | | 424/47 |
| 5,955,066 A * | 9/1999 | Sako et al. | | 424/70.12 |
| 5,997,851 A * | 12/1999 | Cox et al. | | 424/70.1 |
| 6,030,630 A * | 2/2000 | Fleury et al. | | 424/401 |
| 6,083,493 A * | 7/2000 | Swaile | | 424/65 |
| 6,139,849 A * | 10/2000 | Lesaulnier et al. | | 424/401 |
| 6,277,893 B1 * | 8/2001 | Babenko | | 516/67 |
| 6,352,701 B1 * | 3/2002 | Scholz et al. | | 424/405 |
| 6,503,479 B1 * | 1/2003 | LesAulnier et al. | | 424/45 |
| 6,555,099 B2 * | 4/2003 | Guskey et al. | | 424/65 |
| 6,749,837 B1 * | 6/2004 | Samain et al. | | 424/47 |
| 6,808,701 B2 * | 10/2004 | Duden et al. | | 424/70.19 |
| 2002/0015681 A1 * | 2/2002 | Carballada et al. | | 424/45 |
| 2002/0085988 A1 * | 7/2002 | Nambu | | 424/70.19 |
| 2003/0077240 A1 * | 4/2003 | LeGrow et al. | | 424/70.121 |
| 2003/0206871 A1 * | 11/2003 | Sturla et al. | | 424/47 |
| 2003/0219394 A1 * | 11/2003 | Mercier et al. | | 424/70.12 |
| 2004/0005285 A1 * | 1/2004 | Midha | | 424/70.27 |
| 2004/0202622 A1 * | 10/2004 | Quadir | | 424/59 |
| 2005/0048021 A1 * | 3/2005 | Salem et al. | | 424/70.14 |
| 2005/0069516 A1 * | 3/2005 | Hornby et al. | | 424/74 |
| 2005/0176600 A1 * | 8/2005 | Samain et al. | | 510/119 |
| 2005/0186159 A1 * | 8/2005 | Gonzalez et al. | | 424/59 |
| 2005/0220728 A1 * | 10/2005 | Kanji et al. | | 424/59 |
| 2005/0244349 A1 * | 11/2005 | Chaudhuri et al. | | 424/59 |
| 2006/0079415 A1 * | 4/2006 | Kozubal et al. | | 510/119 |
| 2006/0147399 A1 * | 7/2006 | McNamara et al. | | 424/63 |
| 2006/0153891 A1 * | 7/2006 | Gonzalez et al. | | 424/405 |
| 2007/0191548 A1 * | 8/2007 | Chrisstoffels et al. | | 525/242 |
| 2007/0248557 A1 * | 10/2007 | Mason et al. | | 424/70.13 |
| 2007/0292359 A1 * | 12/2007 | Friedman et al. | | 424/47 |
| 2008/0102049 A1 * | 5/2008 | McDermott | | 424/64 |
| 2008/0145350 A1 * | 6/2008 | Popescu et al. | | 424/94.1 |
| 2008/0148495 A1 * | 6/2008 | Quadir | | 8/409 |
| 2008/0193489 A1 * | 8/2008 | De Armond et al. | | 424/400 |
| 2009/0068124 A1 * | 3/2009 | Beumer et al. | | 424/54 |
| 2009/0068136 A1 * | 3/2009 | Beumer et al. | | 424/70.16 |
| 2009/0175799 A1 * | 7/2009 | Tamarkin et al. | | 424/43 |
| 2009/0214608 A1 * | 8/2009 | Monin et al. | | 424/401 |
| 2010/0303931 A1 * | 12/2010 | Feltin et al. | | 424/683 |

FOREIGN PATENT DOCUMENTS

| | | | |
|---|---|---|---|
| EP | 0635257 A | | 1/1995 |
| EP | 0916689 A | | 5/1999 |
| EP | 1306076 A | | 5/2003 |
| EP | 1532968 A | | 5/2005 |
| JP | 07089844 A | | 4/1995 |
| WO | 94/08557 | * | 4/1994 |
| WO | 9933434 A | | 7/1999 |
| WO | 99/55295 | * | 11/1999 |
| WO | 00/06107 | * | 2/2000 |
| WO | 0006107 A | | 2/2000 |

OTHER PUBLICATIONS

English Language Abstract for WO 99/33434.
English Language Abstract for JP 07 089844.
English Language Abstract for EP 1532968.

* cited by examiner

*Primary Examiner* — Charles Boyer
(74) *Attorney, Agent, or Firm* — Norris McLaughlin & Marcus

(57) ABSTRACT

The present invention is related to a hair styling composition for keratin fibers especially for hair comprising at least one film forming polymer and at least one arylated silicone.

11 Claims, No Drawings

HAIR STYLING COMPOSITION COMPRISING AN ARYLATED SILICONE

The present invention is related to hair styling composition for keratin fibres especially for hair.

Aerosol hair styling compositions have been widely used either as a spray or as foam. In principal they comprise hair fixing polymers in an aqueous or aqueous alcoholic medium together with a propellant. Many fixing polymers have been suggested in the literature either synthetic or natural origin. Natural polymers so far suggested do not satisfy the expectations of consumers in terms of hair feel and hold of hair style for a long time and, therefore, overwhelmingly synthetic polymers are used.

The present inventors have surprisingly found out that a composition comprising at least one film forming polymer and at least one arylated silicone in an aqueous, aqueous-alcoholic or alcoholic medium has excellent hair styling and restyling benefits together with excellent volumizing and bodifying effects. The hair feels natural upon touching and looks excellently shiny.

Thus, the object of the present invention is a composition for keratin fibres especially for hair based on an aqueous, aqueous-alcoholic or alcoholic medium comprising at least one film forming polymer and at least one arylated silicone.

Another object of the present invention is the use of a composition based on an aqueous, aqueous-alcoholic or alcoholic medium comprising at least one film forming polymer and at least one arylated silicone for styling and restyling keratin fibres especially hair.

Still another subject of the present invention is a process for styling keratin fibres especially hair wherein a composition based on an aqueous, aqueous-alcoholic or alcoholic medium comprising at least one film forming polymer and at least one arylated silicone is applied onto wet and/or dry hair and hair is styled without rinsing off the composition.

With the term styling it is meant that the hair is freshly styled. With the term restyling it is meant that hair is already styled with an aqueous, aqueous-alcoholic or alcoholic composition of the present invention and after lapse of certain period of time a new style is given without using further composition of the present invention.

Thus, further object of the present invention is a process for restyling hair wherein keratin fibres especially hair already styled with an aerosol composition based on an aqueous, aqueous-alcoholic or alcoholic medium comprising at least one natural starch and at least propellant is with or without wetting a new style is given.

The compositions of the present invention comprises at least one arylated silicone at a concentration range of 0.01 to 5%, preferably 0.05 to 4% more preferably 0.1 to 3% and most preferably 0.1 to 2.5% by weight calculated to total composition. Non-limiting suitable examples are phenyl methicone, phenyl trimethicone, diphenyl dimethicone, diphenylsiloxy phenyl trimethicone, tetramethyl tetraphenyl trisiloxane, triphenyl trimethicone, tetramethyl tetraphenyl trisiloxane and trimethyl pentaphenyl trisiloxane.

In the preferred embodiment of the present invention, the arylated silicone comprises at least 2 phenyl groups, more preferably 3 and most preferably 5 phenyl groups in its molecule.

Particularly preferred arylated silicone is trimethyl pentaphenyl trisiloxane available from Dow Corning under the trade name DC PH-1555 HRI.

It should be noted that compositions of the present invention can also comprise more than one arylated silicone.

Compositions of the present invention comprise at least one film forming polymer at a concentration of 0.1 to 25%, preferably 1.5 to 20%, more preferably 2.5 to 15 and most preferably 4 to 15% by weight calculated to total composition.

Within the meaning of the present invention at least one film forming polymer is selected from the anionic, non-ionic, cationic and/or amphoteric or zwitterionic ones. Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64, Plus from BASF AG and advantage LS-E from ISP.

Natural non-ionic polymers are as well suitable for the composition of the present invention. Those are such as cellulose, chitosan, guar gum, neutralised shellac and their derivatives.

As amphoteric polymers which can be used alone or in mixture with at least one additional nonionic polymer, reference is here made in particular to copolymers of N-octyl acrylamide, (meth)acrylic acid and tert.-butyl aminoethyl methacrylate of the type "Amphomer®"; copolymers from methacryloyl ethyl betaine and alkyl meth-acrylates of the type "Yukaformer®", e.g. the butyl methacrylate copolymer "Yukaformer® Am75"; copolymers from monomers containing carboxyl groups and sulfonic groups, e.g. (meth)acrylic acid and itaconic acid, with monomers such as mono- or dialkyl aminoalkyl(meth)acrylates or mono- or dialkyl aminoalkyl(meth)-acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199.

Suitable anionic polymers alone or in combination with non-ionic polymers are vinyl-alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide co-polymers of the type "Ultrahold®"; vinyl pyrrolidone/vinyl acetate/itaconic acid co-polymers, acrylic acid/acrylamide copolymers or the sodium salts thereof of the type "Reten®"; etc.

Further suitable anionic polymers are Acrylate copolymers available under trade name Salcare SC 81, PEG/PPG 25/25 dimethicone/acrylate copolymer available under trade name Luviglex Silk from BASF, Acrylates/t-butylacrylamide copolymer available under trade name Ultrahold Strong, Advantage LC-E which is vinylcaprolactam/PVP/dimethylaminoethylmethacrylate copolymer and VA/crotonates copolymer available under trade name Luviset CA 66.

Composition of the present invention can comprise cationic polymers alone or in combination with non-ionic polymer. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore chitosan and chitin can also be included in the compositions as cationic natural polymers.

Furthermore, those cationic polymers known with their CTFA category name Polyquaternium may as well be added into the compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 24, Polyquaternium 67, and Polyquaternium 72.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643. Among these especially preferred is the compound know with the INCI name Polysilicone-9.

In further preferred embodiment of the present invention, composition can comprise at least one natural starch. Preferred are wheat, rice, potato, corn starches. Most preferred is rice starch and at a concentration of 0.1 to 25%, preferably 1.5 to 20%, more preferably 2.5 to 15 and most preferably 4 to 15% by weight calculated to total composition.

In further preferred embodiment of the present invention, the compositions comprises at least one synthetic or natural oil. In principal, any oil allowed for cosmetic use is suitable for the compositions of the present invention.

Oils are those of synthetic and of natural ones. Natural oils are in principal any triglyceride suitable for cosmetic use. Non-limiting examples are avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or also olive oil, soya oil, and the derivatives thereof. Mineral oils such as paraffin oil and petrolatum are suitably contained within the scope of the present invention. It should as well be noted that compositions of the present invention can contain mixture of one or more natural oils and mineral oil.

Further, suitable synthetic oil components are in particular fatty alcohol fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters, cetyl palmitate, etc.

Synthetic ones are those of silicone oils. Here again any silicone oil either volatile and/or non-volatile is suitable for the compositions of the present invention. Preferred silicone oils are non-volatile silicone oils known with their INCI name as dimethicone and dimethiconol. Volatile silicone oils such as cyclomethicones may be used in combination with non-volatile silicones and/or other wax and/or oils mentioned above. Commercially, they are available from various companies for example Dow Corning with the known DC series, Wacker Chemie and Toray silicones. All commercially available non volatile silicones are suitable in the compositions of the present invention. Examples to those are DC 200 series, DC1401, DC 1403, DC 1501 and DC 1503.

Concentration of one or more oil in the compositions of the present invention is between 0.01 and 10%, preferably 0.05 and 7.5% more preferably 0.1 and 5% and most preferably 0.25 and 2.5% by weight calculated to total composition.

Compositions of the present invention may also comprise wax. Suitable and preferred examples are petrolatum, ozokerit, carnauba wax, paraffin, lanolin wax, candelila wax, bees wax, microcrystalline wax and cocoglycerides. Concentration of wax may be in the range of 0.01 to 10%, preferably 0.05 to 5% by weight calculated to total composition.

Compositions of the present invention may comprise one or more surfactant for solubilising of one or more ingredients not soluble in the medium used or especially for the foam aerosol composition for achieving required foam especially the styling polymer when present does not have such properties. Suitable ones are of anionic, non-ionic, amphoteric and cationic surfactants or their mixtures.

As a rule any cationic surfactant is suitable for the compositions of the present invention. Preferably at least one cationic surfactant is selected from the compounds with the general formula

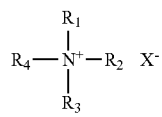

where $R_1$ s a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and and $R_2$, $R_3$ and $R_4$ are independent from each other H or lower alkyl chain with 1 to 4 carbon atoms or ethoxy or propoxy group with number of ethoxy or propoxy groups varying in the range of 0 to 4, and X is chloride, bromide or methosulfate.

Non-limiting examples to suitable cationic surfactants are cetyl trimethyl ammonium chloride, myristoyl trimethyl ammonium chloride, behentrimonium chloride, trimethyl cetyl ammonium bromide, stearyl trimethyl ammonium chloride, dimethyl stearyl ammonium chloride, stearamidopropyldimethyl ammonium chloride.

Suitable non-ionic surfactants are alkyl polyglucosides of the general formula

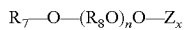

wherein $R_7$ is an alkyl group with 8 to 18 carbon atoms, $R_8$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid mono and di ethanolamide and myristic fatty acid mono and di ethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants useful in the compositions according to invention are $C_{10}$-$C_{22}$-fatty alcohol ethoxylates. Suitable non-limiting examples are oleth-10, oleth-11, oleth-12, oleth-15, oleth-16, oleth-20, oleth-25, oleth-30, oleth-35, oleth-40, laureth-10, laureth-11, laureth-12, laureth-13, laureth-15, laureth-16, laureth-20, laureth-25, laureth-30, laureth-35, laureth-40, laureth-50, ceteth-10, ceteth-12, ceteth-14, ceteth-15, ceteth-16, ceteth-17, ceteth-20, ceteth-25, ceteth-30, ceteth-40, ceteth-45, cetoleth-10, cetoleth-12, cetoleth-14, cetoleth-15, cetoleth-16, cetoleth-17, cetoleth-20, cetoleth-25, cetoleth-30, cetoleth-40, cetoleth-45, ceteareth-10, ceteareth-12, ceteareth-14, ceteareth-15, ceteareth-16, ceteareth-18, ceteareth-20, ceteareth-22, ceteareth-25, ceteareth-30, ceteareth-40, ceteareth-45, ceteareth-50, isosteareth-10, isosteareth-12, isosteareth-15, isosteareth-20, isosteareth-22, isosteareth-25, isosteareth-50, steareth-10, steareth-11, steareth-14, steareth-15, steareth-16, steareth-20, steareth-25, steareth-30, steareth-40, steareth-50, steareth-80 and steareth-100. Additional examples of similar compounds can be found in the cosmetic ingredient dictionaries and cosmetic textbooks.

Further non-ionic surfactants within the meaning of the present invention are polyalkyleneglycol ether of fatty acid glyceride or partial glyceride with at least 30 polyalkylene units are with 30 to 1000, preferably 30 to 500, more preferably 30 to 200 and most preferably 40 to 100 polyethyleneglycol units. Examples to those are PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil, PEG-200 castor oil. Additional examples of similar compounds can be found in the cosmetic ingredient dictionaries and cosmetic textbooks.

Further suitable non-ionic surfactants are monoglycerides such as glyceryl stearate, glyceryl palmitate, glyceryl myristate, glyceryl behenate.

As further surfactant component, the compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate.

Further, suitable within the meaning of the present invention are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride(ether)sulfates, fatty acid amide sulfates obtained by ethoxylation and subsequent sulfatation of fatty acid alkanolamides, and the alkali salts thereof, as well as the salts of long-chain mono-, di- or tri alkyl phosphates.

Additional anionic surfactants useful are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

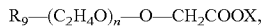

wherein $R_9$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Concentration of one or more surfactant in the compositions according to present invention is in the range of 0.01 to 5%, preferably 0.05 to 2.5% and more preferably 0.1 to 1% by weight calculated to total composition. Preferred surfactants are non-ionic, amphoteric and cationic ones. The most preferred is non-ionic surfactants.

The composition of the present invention may comprise polyols at a concentration of 0.5 to 15%, preferably 1 to 10%, more preferably 2 to 5% by weight calculated to the total concentration. The most preferred ones are glycerine, propylene glycols, butylene glycol and hexylene glycol.

The compositions according to the invention may also comprise further agents, such as proteins, for example bamboo protein, and protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 5%, preferably 0.05% to 3.5%, in particular 0.1% to 2% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis". $4^{th}$ Ed.

Compositions of the present invention may contain UV filters either for stabilization of the product colour and/or for protection of hair from environmental influences such as loss of elasticity, loss of hair colour (bleaching effect of sun light). Suitable UV-absorbing substance are Polysilicone-15, 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher, and/or polysiliocne-15.

The suitable amount of the UV-absorber ranges from about 0.01% to 1% by weight, calculated to the total composition. Attention should be paid to the stability and solubility especially when using UV filter as salts, e.g. anionic UV filter salts.

The compositions of the present invention can contain one or more organic solvents within the scope of the invention. Suitable ones are ethanol, propanol, isopropanol, isopentane, n-pentane, n.hexane, dimethoxymethane, benzyl alcohol, benzyloxyethanol, alkylene carbonates such as ethylene carbonate and propylene carbonate, phenoxyethanol, butanol, isobutanol, cyclohexane, cyclohexanol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. The most preferred organic solvents are ethanol, isopropanol and propanol. Concentration of solvents is in the range of 0 to 80% and preferably 5 to 70%, more preferably 10 to 60% and most preferably 10 to 50% by weight calculated to total composition.

Compositions of the present invention may further comprise polyethyleneglycols Suitable non-limiting examples are PEG-14, PEG-20, PEG-23, PEG-25, PEG-90, PEG-115, PEG-160, PEG-14M, PEG-20M, PEG-23M, PEG-25M, PEG-90M, PEG-115M, PEG-160M, etc. Concentration of the high molecular weight polyethyleneglycol, one or mixture of more than one, is in the range of 0.05% to 2.5%, preferably 0.1% to 1.5% and most preferably between 0.1 to 1.0% by weight calculated to total composition.

In a further embodiment of the present invention, the compositions comprise at least one direct dye for colouring hair. Suitable direct dyes are cationic, anionic, neutral dyes and their mixtures as available commercially from various suppliers and used mainly in semipermanent hair coloration.

Non-limiting examples to cationic dyes are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Further suitable direct dyes are anionic dye. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. When using direct dyes of various categories, their compatibility must be checked.

The above mentioned dyestuffs are also used especially the anionic ones for product colouring at reduced concentrations.

Concentration of direct dyes in the compositions of the present invention is within the range of 0.001 to 5%, preferably 0.01 to 3% and more preferably 0.05 to 2%, and most preferably 0.1 to 1% by weight calculated to total composition, calculated to total composition.

In case an aerosol type of styling product is designed then composition of the present invention comprises additionally at least one propellant.

Compositions of the present invention comprises at least one propellant at a concentration of 5 to 60%, preferably 5 to 50% more preferably 10 to 50% by weight calculated to total composition. Suitable propellants are lower alkanes such as n-butane, i-butane, propane, butane or their mixtures, as well as dimethylether (DME) either alone or in mixture with lower alkanes. Further suitable propellants are fluorinated hydrocarbons such as 1,1-difluoro ethane or tetrafluoroethane or their mixtures with each other, carbon dioxide and nitogen or their mixtures with the above mentioned propellants. Preferred are lower alkanes such as propane, butane, n-butane, i-butane, and their mixtures and their mixture with DME at a alkane to DME weight ratio 10:1 to 1:10.

Furthermore compositions of the present invention can comprise all substances customarily found in such preparations. Examples of such substances are complexing agents, preservatives, fragrances, etc.

The following examples are to illustrate the invention but not to limit.

EXAMPLE 1

Hair Spray

|  | % by weight |
|---|---|
| Trimethyl pentaphenyl trisiloxane | 1.50 |
| VP/VA copolymer | 10.00 |
| Fragrance | q.s. |
| Ethanol | q.s to 100% |

The above composition was prepared by dissolving—dispersing all ingredients one by one in ethanol.

The above composition was filled into an aerosol can with 55% by weight bulk, 40% by weight propane/butane and 5% by weight dimethylether, all values are calculated to total composition.

The hair styled with the above composition is excellently styled and has excellent shine.

EXAMPLE 2

| Pumpspray | |
|---|---|
|  | % |
| Ethanol | 90.0 |
| Polyquaternium-11 | 0.2 |
| Polyvinylcaprolactam | 1.0 |
| Trimethyl pentaphenyl trisiloxane | 0.1 |
| Fragrance | 0.2 |
| PEG-40 Hydrogenated Castor oil | 0.4 |
| Water | add 100.0 |

Polymers are dissolved in ethanol, fragrance and Trimethyl pentaphenyl trisiloxane is dissolved/mixed first with PEG-40 hydrogenated castor oil and than added to the solution of polymers in ethanol. Finally, the composition is made up to 100% by adding water.

EXAMPLE 3

| Aerosolspray | |
|---|---|
| Ethanol | 37.0 |
| PVP (Luviskol K 30) | 0.25 |
| Vinylacetate/crotonic acid copolymer | 3.6 (Aristoflex A 60) |
| Trimethyl pentaphenyl trisiloxane | 0.15 |
| Fragrance | 0.2 |
| Water | 34.1 |
| Dimethylether | 38.0 |
| n-pentane | 12.0 |
| Neutralizing agent | q.s. pH 8.0 |

The composition is prepared in the same way as in Example 2.

EXAMPLE 4

| Pumpspray | |
|---|---|
|  | % by weight |
| PVP (Luviskol K 90) | 0.3 |
| Acrylates/Octylacrylamide Copolymer | 1.0 |
| Aminomethyl Propanol | 0.25 |
| Trimethyl pentaphenyl trisiloxane | 0.15 |
| Fragrance | 0.2 |
| Ethanol | add 100 |

The composition is prepared in the same way as in Example 2.

EXAMPLE 5

| Pumpspray | |
|---|---|
|  | % by weight |
| Polyquaternium-11 | 0.25 |
| VP/VA Copolymer ((Luviskol VA 64W) | 2.0 |
| Trimethyl pentaphenyl trisiloxane | 0.2 |
| Ethanol | 40 |
| Fragrance | 0.2 |
| PEG-40 Hydrogenated Castor oil | 0.5 |
| Water | add 100 |

The composition is prepared in the same way as in Example 2.

EXAMPLE 6

| Pumpspray | |
|---|---|
|  | % |
| Shellac (neutralized) | 1.0 |
| PVP | 0.2 |
| Trimethyl pentaphenyl trisiloxane | 0.3 |
| Octylmethoxycinnamate | 0.3 |
| Fragrance | 0.2 |
| Water | 10.0 |
| Ethanol | add 100 |

The composition is prepared in the same way as in Example 2.

EXAMPLE 7

| Pumpspray | |
|---|---|
|  | % |
| Chitosan | 0.1 |
| VP/VA Copolymer (Luviskol VA 64W) | 2.0 |

-continued

| Pumpspray | |
|---|---|
| | % |
| Trimethyl pentaphenyl trisiloxane | 0.5 |
| Fragrance | 0.2 |
| PEG-40 Hydrogenated castor oil | 0.2 |
| Ethanol | 10 |
| Water | add 100% |

The composition is prepared in the same way as in Example 2.

EXAMPLE 8

| Styling gel | |
|---|---|
| | % |
| PVP (Luviskol K 90) | 4.0 |
| VP/VA Copolymer (Luviskol VA 64W) | 4.0 |
| Panthenol | 0.5 |
| Trimethyl pentaphenyl trisiloxane | 0.5 |
| PEG-40 Hydrogenated castor oil | 0.5 |
| Glycerol | 10.0 |
| Ethanol | 10.0 |
| Fragrance, preservative | q.s. |
| Neutralizing agents | q.s to pH 6.0 |
| Water | add 100 |

EXAMPLE 9

| Styling gel | |
|---|---|
| | % |
| Acrylates/Octylacrylamide copolymer | 2.0 (Amphomer HC) |
| VP/VA Copolymer (Luviskol VA 64W) | 8.0 |
| Acrylates/C10-30 cetyl acrylate Crosspolymer | 0.6 |
| Panthenol | 0.5 |
| Trimethyl pentaphenyl trisiloxane | 0.4 |
| PEG-40 Hydrogenated castor oil | 0.4 |
| Propylene glycol | 5.0 |
| Ethanol | 10.0 |
| Fragrance, preservative | q.s. |
| Neutralizing agents | q.s to pH 6.5 |
| Water | ad 100 |

EXAMPLE 10

| Styling mousse | |
|---|---|
| | % by weight |
| Polyquaternium-11 | 2.0 (Gafquat 440) |
| VP/VA Copolymer (Luviskol VA 64W) | 4.0 |
| Cetrimonium chloride | 0.4 |
| Laureth-23 | 0.2 |
| Trimethyl pentaphenyl trisiloxane | 0.5 |
| PEG-40 Hydrogenated castor oil | 0.5 |
| Ethanol | 5.0 |

-continued

| Styling mousse | |
|---|---|
| | % by weight |
| Fragrance, preservative | q.s. |
| Water | ad 100 |

The composition is prepared in the same way as in Example 2. The solution is filled into an aerosol can with a propellant mixture of propane/butane at a liquid composition to propellant ratio of 90:10.

EXAMPLE 11

| Styling mousse | |
|---|---|
| | % by weight |
| Polyquaternium-46 | 4.0 (Luviquat Hold) |
| VP/VA Copolymer (Luviskol VA 64W) | 8.0 |
| Dicocoylethyl hydroxyethylmonium methosulfate | 0.6 |
| Laureth-23 | 0.3 |
| Trimethyl pentaphenyl trisiloxane | 0.3 |
| PEG-40 Hydrogenated castor oil | 0.2 |
| Benzophenone-3 | 0.3 |
| Ethanol | 5.0 |
| Fragrance, preservative | q.s. |
| Water | ad 100 |

The composition is prepared in the same way as in Example 1. The solution is filled into an aerosol can with a propellant mixture of propane/butane at a liquid composition to propellant ratio of 95:5.

EXAMPLE 12

| Pump spray for damaged hair | |
|---|---|
| PVP (Luviskol K 90) | 0.3 |
| Acrylates/Octylacrylamide Copolymer | 1.0 |
| Aminomethyl Propanol | 0.25 |
| Trimethyl pentaphenyl trisiloxane | 0.05 |
| Behenic acid | 0.1 |
| Avocadin | 0.05 |
| Fragrance | 0.2 |
| PEG-40 Hydrogenated castor oil | 0.2 |
| Ethanol | add 100 |

EXAMPLE 13

| Aerosol spray | |
|---|---|
| PVP (Luviskol K 90) | 2.5 |
| PEG/PPG-25/25 Dimethicne acrylates copolymer | 2.5 |
| Aminomethyl Propanol | q.s |
| Trimethyl pentaphenyl trisiloxane | 0.1 |
| Polysilicone-9 | 0.2 |
| Fragrance | 0.2 |
| PEG-40 Hydrogenated castor oil | 0.4 |
| Ethanol | add 100 |

The above composition is filled at a weight ratio of 60 to 40 lotion to propellant mixture of Dimethylether and n-Pentane (1:1)

EXAMPLE 14

| Aerosol spray | |
|---|---|
| VP/VA | 2.5 |
| Acrylates octylacrylamide copolymer | 5.0 |
| Aminomethyl Propanol | q.s |
| Trimethyl pentaphenyl trisiloxane | 0.5 |
| Polysilicone-9 | 0.5 |
| Ethylmethoxycinnamate | 0.1 |
| Fragrance | 0.2 |
| PEG-40 Hydrogenated castor oil | 0.5 |
| Ethanol | add 100 |

The above composition is filled at a weight ratio of 45 to 55 lotion to propellant mixture of n-Pentane and Difluoro ethane (10:45)

EXAMPLE 15

| Aerosol spray | |
|---|---|
| Acrylates T-butylacrylamide copolymer | 14.0 |
| Aminomethyl Propanol | q.s |
| Trimethyl pentaphenyl trisiloxane | 0.15 |
| Polysilicone-9 | 0.3 |
| Ethylmethoxycinnamate | 0.1 |
| Fragrance | 0.2 |
| PEG-40 Hydrogenated castor oil | 0.4 |
| Ethanol | add 100 |

The above composition is filled at a weight ratio of 55 to 45 lotion to propellant of n-Pentane.

EXAMPLE 16

| Styling Gel | |
|---|---|
| VP/VA copolymer | 5.0 |
| Acrylates octylacrylamide copolymer | 1.0 |
| Acrylates/Palmeth-25 Acrylate Copolymer | 2.5 |
| Aminomethyl Propanol | q.s |
| Trimethyl pentaphenyl trisiloxane | 0.3 |
| Polysilicone-9 | 0.3 |
| Benzophenone-3 | 0.1 |
| Panthenol | 0.3 |
| Fragrance | 0.2 |
| PEG-40 Hydrogenated castor oil | 0.5 |
| Ethanol | 10.0 |
| Water | add 100 |

EXAMPLE 17

| Styling Gel | |
|---|---|
| Acrylates octylacrylamide copolymer | 5.0 |
| Acrylates/Palmeth-25 Acrylate Copolymer | 2.0 |
| Acrylates copolymer | 2.0 |
| Aminomethyl Propanol | q.s |
| Trimethyl pentaphenyl trisiloxane | 0.1 |
| Benzophenone-3 | 0.1 |
| Panthenol | 0.3 |
| Fragrance | 0.2 |
| PEG-40 Hydrogenated castor oil | 0.2 |
| Ethanol | 15 |
| Water | add 100 |

EXAMPLE 18

| Styling Gel | |
|---|---|
| Acrylates/Palmeth-25 Acrylate Copolymer | 1.0 |
| Acrylates copolymer | 3.0 |
| Aminomethyl Propanol | q.s |
| Trimethyl pentaphenyl trisiloxane | 0.2 |
| Benzophenone-3 | 0.1 |
| Panthenol | 0.3 |
| Fragrance | 0.2 |
| PEG-40 Hydrogenated castor oil | 0.2 |
| Ethanol | 15 |
| Water | add 100 |

EXAMPLE 19

| Mousse | |
|---|---|
| Polyquaternium-16 | 1.5 |
| VP/VA | 3.0 |
| Aminomethyl propanol | q.s |
| Trimethyl pentaphenyl trisiloxane | 1.0 |
| Panthenol | 0.3 |
| Fragrance | 0.2 |
| PEG-40 Hydrogenated castor oil | 0.3 |
| Ethanol | 5 |
| Water | add 100 |

The above formulation was filled with propane/butane as a propellant at a weight ratio of lotion to propellant of 90/10.

EXAMPLE 20

| Mousse | |
|---|---|
| Polyquaternium-11 | 0.3 |
| Polyqauternium-4 | 0.2 |
| VA Crotanes copolymer | 1.0 |
| Aminomethyl propanol | q.s |
| Trimethyl pentaphenyl trisiloxane | 1.0 |
| Ethylhexylmethoxycinnamate | 0.1 |
| Panthenol | 0.5 |
| Fragrance | 0.2 |
| PEG-40 Hydrogenated castor oil | 0.2 |
| Ethanol | 12 |
| Water | add 100 |

The above formulation was filled with propane/butane as a propellant at a weight ratio of lotion to propellant of 92/8.

EXAMPLE 21

| Mousse | |
|---|---|
| Polyquaternium-46 | 0.6 |
| VP/VA | 8.0 |
| Aminomethyl propanol | q.s |
| Trimethyl pentaphenyl trisiloxane | 0.1 |
| Laureth-23 | 0.1 |
| Ethylhexylmethoxycinnamate | 0.1 |
| Panthenol | 0.5 |
| Fragrance | 0.2 |
| PEG-40 Hydrogenated castor oil | 0.2 |
| Ethanol | 18 |
| Water | add 100 |

The above formulation was filled with propane/butane as a propellant at a weight ratio of lotion to propellant of 92/8.

EXAMPLE 22

| Hair Wax | |
|---|---|
| | % by weight |
| Mineral oil | 3.0 |
| Paraffin | 10.0 |
| Cetearyl alcohol | 2.0 |
| Ceteareth-20 | 4.0 |
| VP/VA | 6.0 |
| Glyceryl stearate | 3.0 |
| Acrylates/Palmeth-25 Acrylate Copolymer | 1.0 |
| Trimethyl pentaphenyl trisiloxane | 1.0 |
| Polysilicone-9 | 1.0 |
| Fragrance, preservative, dye | q.s. |
| Water | to 100 |

EXAMPLE 23

| Hair Wax | |
|---|---|
| | % by weight |
| Ceteareth-3 | 20.0 |
| Candelila cera | 5.0 |
| Petrolatum | 40.0 |
| Glyceryl stearate | 3.0 |
| VP/VA | 6.0 |
| Trimethyl pentaphenyl trisiloxane | 1.6 |
| Polysilicone-9 | 1.0 |
| Fragrance, preservative, dye | q.s. |
| Water | to 100 |

The invention claimed is:

1. An aerosol spray or foam styling composition for keratin fibres especially for human hair comprising an aqueous, aqueous—alcoholic or alcoholic medium, between about 1.5 to 25% by weight of at least one film forming polymer selected from the group consisting of homo- and copolymers of vinylpyrrolidone, at least one cationic polymer selected from the group consisting of polyquaterinum-11; polyquaternium-4; polyquaternium-16; polyquaternium-46; and polysilicone-9; between about 0.01 to less than 5% by weight of at least one arylated silicone selected from the group consisting of diphenyl dimethicone, diphenylsiloxy phenyl trimethicone, tetramethyl tetraphenyl trisiloxane, triphenyl trimethicone, tetramethyl tetraphenyl trisiloxane and trimethyl pentaphenyl trisiloxane, and between about 5 to 60% by weight of at least one propellant.

2. The composition according to claim 1 wherein the arylated silicone is trimethyl pentaphenyl trisiloxane.

3. The composition according to claim 1 comprising at least two arylated silicones.

4. The composition according to claim 1 further comprising at least one synthetic or natural oil present at a concentration of 0.1 to 10% by weight calculated to total concentration.

5. The composition according to claim 1 further comprising at least one wax present at a concentration of 0.01 to 10% by weight calculated to total concentration.

6. The composition according to claim 1 further comprising an organic solvent.

7. The composition according to claim 1 further comprising at least one surfactant selected from the group consisting of anionic, cationic, non-ionic and amphoteric surfactants.

8. The composition according to claim 1 further comprising at least one UV filter.

9. The composition according to claim 1 further comprising at least one direct dye.

10. The composition according to claim 1 further comprising at least one natural starch selected from the group consisting of wheat, rice, potato and corn starches and mixtures thereof, and present at a concentration of 0.1 to 25% by weight calculated to total composition.

11. The composition according to claim 1 wherein the propellant is selected from the group consisting of n-butane, i-butane, butane, propane, 1,1 difluoroethane, tetrafluoroethane and dimethylether and mixtures thereof.

* * * * *